(12) United States Patent
Groop et al.

(10) Patent No.: US 10,441,763 B2
(45) Date of Patent: Oct. 15, 2019

(54) STERILE APPLICATOR ASSEMBLY

(71) Applicant: Esthetic Education LLC, Scottsdale, AZ (US)

(72) Inventors: Kristin Groop, Scottsdale, AZ (US); Lawrence Groop, Scottsdale, AZ (US)

(73) Assignee: Esthetic Education LLC, Scottsdale, AZ (US)

( * ) Notice: Subject to any disclaimer, the term of this patent is extended or adjusted under 35 U.S.C. 154(b) by 0 days.

(21) Appl. No.: 15/978,928

(22) Filed: May 14, 2018

(65) Prior Publication Data

US 2019/0151637 A1  May 23, 2019

Related U.S. Application Data

(60) Provisional application No. 62/588,233, filed on Nov. 17, 2017.

(51) Int. Cl.
*A61M 35/00* (2006.01)
*A61M 3/02* (2006.01)

(52) U.S. Cl.
CPC ........ *A61M 35/003* (2013.01); *A61M 3/0254* (2013.01); *A61M 3/0291* (2013.01)

(58) Field of Classification Search
CPC .. A61M 1/0084; A61M 1/008; A61M 3/0279; A61M 3/0254; A61M 5/345; A61M 11/007; A61M 35/003; A61M 3/0291; A61F 11/006; A61J 1/2096; A61B 2017/320072; A61C 17/043; B05C 17/00593
See application file for complete search history.

(56) References Cited

U.S. PATENT DOCUMENTS

| | | | | |
|---|---|---|---|---|
| 1,467,242 | A * | 9/1923 | Elstein | A61M 3/0279 604/104 |
| 6,238,120 | B1 * | 5/2001 | Mark | A45D 19/02 401/134 |
| 6,439,241 | B2 * | 8/2002 | Berke | A45D 34/04 132/200 |
| 8,857,004 | B1 * | 10/2014 | Luis | A46B 9/045 15/159.1 |
| 8,938,841 | B1 * | 1/2015 | Ramirez | A46B 9/045 15/106 |
| 2016/0279342 | A1 * | 9/2016 | Park | A61M 5/3243 |

* cited by examiner

*Primary Examiner* — Tatyana Zalukaeva
*Assistant Examiner* — Gabriella E Burnette
(74) *Attorney, Agent, or Firm* — Joseph W Mott; Hartman Titus PLC

(57) ABSTRACT

A soft tip applicator with flexible tendrils attaches to a syringe for spreading expressed liquid from the syringe onto a surface, such as skin. A detachable connector engages a cannula hub allowing liquid to be drawn into the syringe for later expulsion onto the surface.

5 Claims, 6 Drawing Sheets

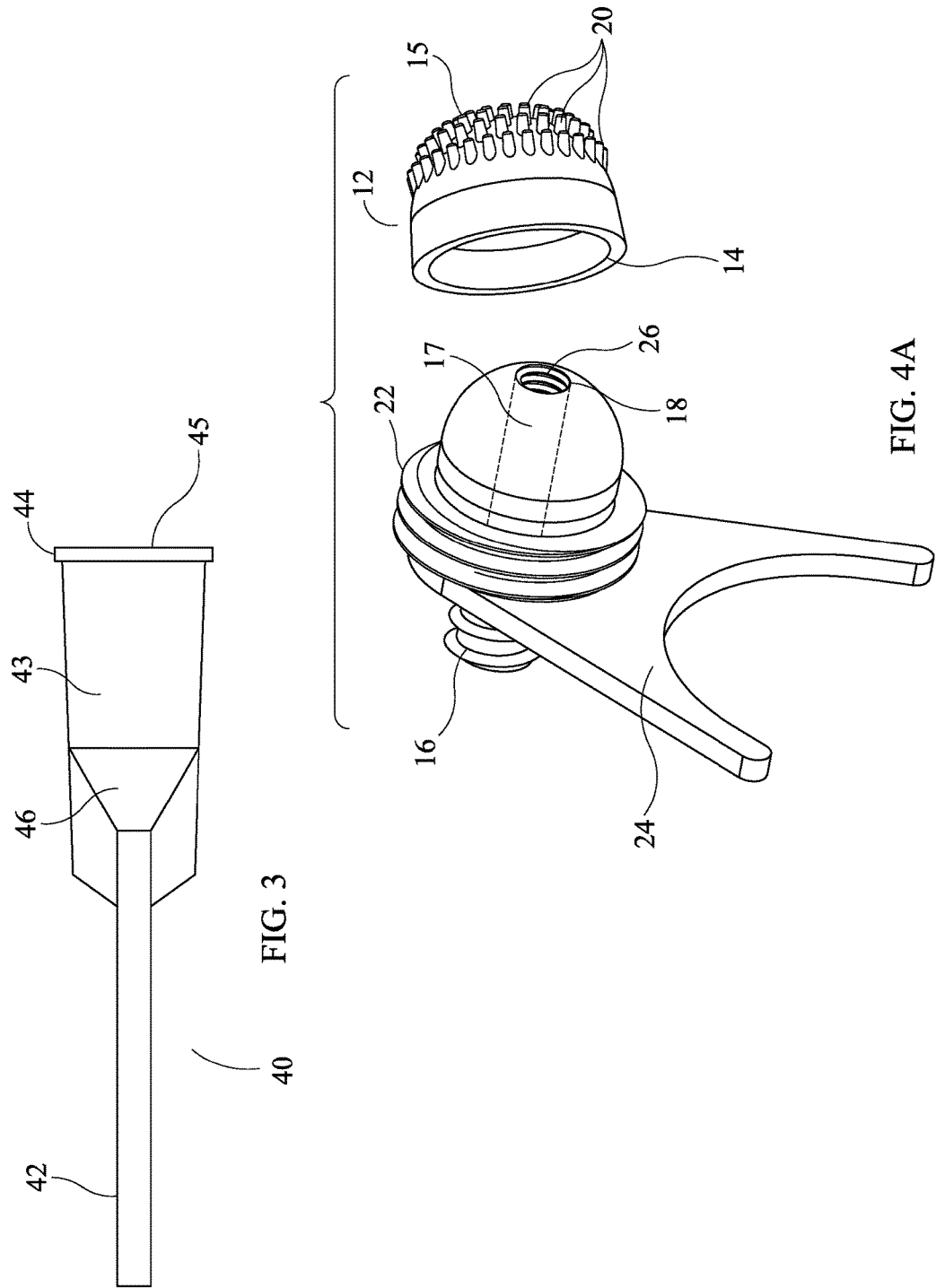

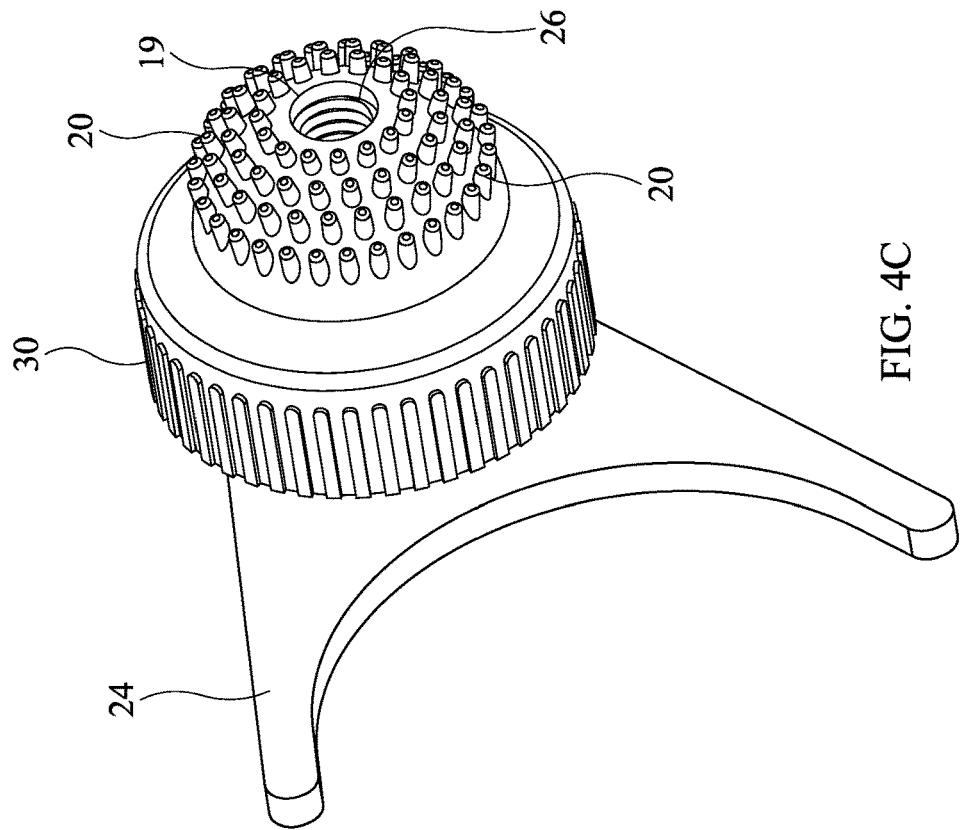
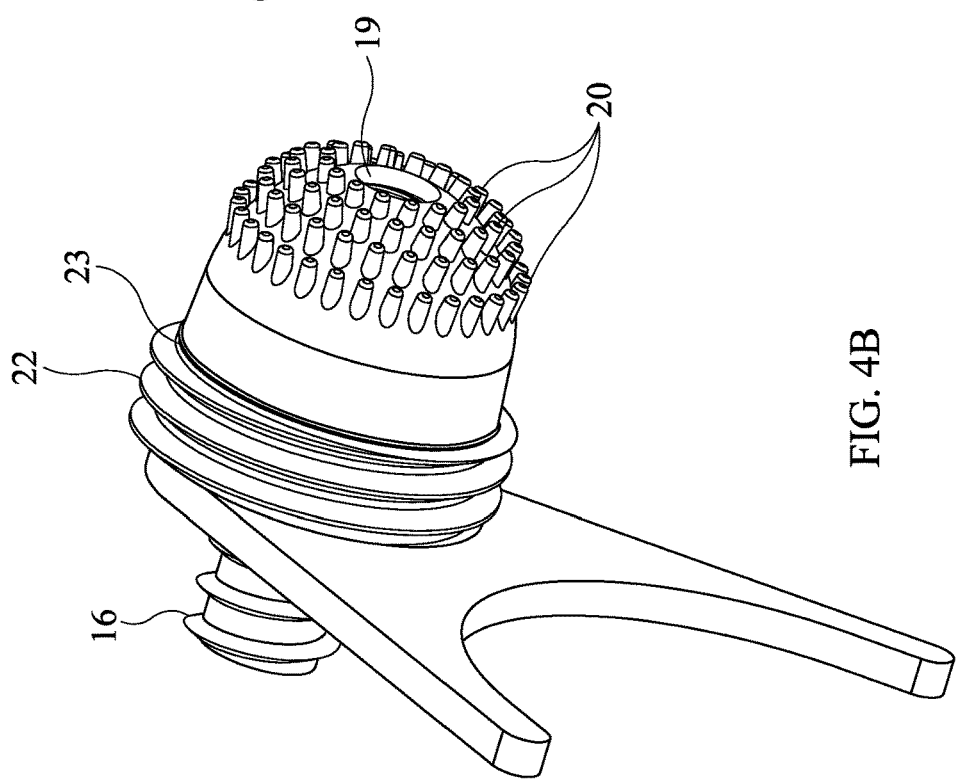
FIG. 4C
FIG. 4B

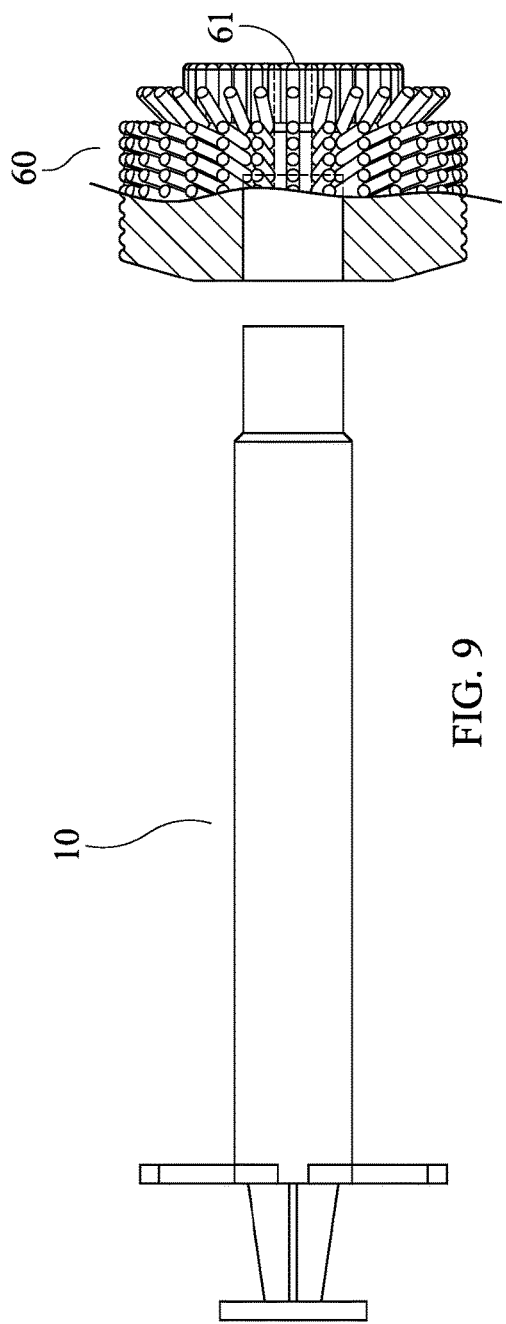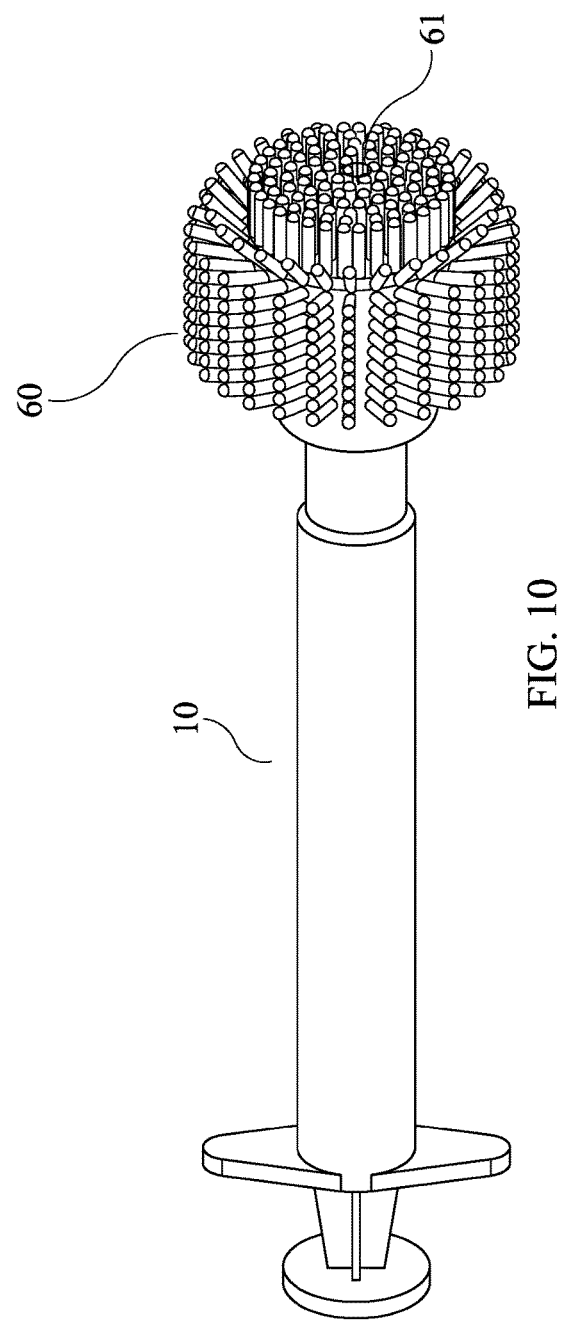
FIG. 9
FIG. 10

STERILE APPLICATOR ASSEMBLY

CROSS REFERENCE TO RELATED APPLICATIONS

This application claims the benefit of U.S. provisional patent application 62/588233, filed Nov. 17, 2017.

TECHNICAL FIELD OF THE INVENTION

The disclosed device relates to effective and sanitary preparation and distribution of treatment liquids, particularly those for use on skin surfaces.

BACKGROUND OF THE INVENTION

Currently, when clinicians perform PRP (Platelet Rich Plasma) treatments, they withdraw blood from the patient's vein, spin it in a centrifuge to separate the blood components, discard the majority of the blood products and keep only the thin layer of platelet rich plasma. The clinician then uses a syringe with a cannula to suction this layer into the syringe. At this point, the clinician may mix this PRP with a stem cell liquid or other liquid component in the barrel of the syringe. This entire process involves having the blood product come into contact with containers and syringes that have been sterilized. The clinician can then either 1) inject this liquid into the skin with a hypodermic syringe or 2) express the liquid (squirt it out) onto the skin.

For clinicians performing the latter, the process now involves evenly distributing the liquid that has been expressed onto the skin. This raises a contamination issue. Currently, clinicians use a gloved finger to rub and distribute the liquid product onto the skin. The gloves that are worn are not sterile. Observation of a demonstration of PRP hair and face restorative procedures by a highly respected plastic surgeon revealed that she used her glove finger to rub and distribute blood product. This introduced contaminants into the process.

It would be desirable to have a sterile applicator to distribute liquid product onto a patient's skin. The applicator should perform a few functions and also give the clinician options. First, the applicator must be sterile. As the barrel syringe is a common item that comes in a sterile package, the applicator must have all the components that attach to the barrel syringe sterilized and packaged in a sealed pouch.

In many cases, a 20 gauge cannula is used to draw liquid into the syringe. However, there are times when certain centrifuge kits have their own cannula provided. An applicator system may include a sterile removable cannula that is distal to the tip of the applicator.

The applicator must be soft to the skin but firm enough to effectively spread the liquid. At the same time, it should be non-absorbent so that expensive product is not wasted during use.

The entire assembly of cannula, connector, applicator, and its connection to the syringe must have a continuous lumen so liquid can be drawn from the distal cannula tip into the syringe. Further, the applicator could also be used to express expensive biologics, drugs, or cosmetic liquids that have previously been drawn into a syringe or are actually packaged in a syringe. As most syringes incorporate a standard luer lock, an embodiment of the applicator incorporates a standard luer lock connection.

SUMMARY OF THE DISCLOSURE

An applicator assembly is provided that attaches to a syringe, which may be a standard barrel syringe, with a lumen that runs from the syringe to an exit aperture in the tip of a soft polymer applicator. In an embodiment, a nub attaches to the syringe and a soft silicone applicator stretches over the nub. A connector interfaces between the nub and a cannula hub with attached cannula. The assembly allows fluid to be drawn through the cannula into the syringe and then, with the cannula removed, expressed onto a surface and spread by the applicator.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which:

FIG. 3 is a detailed view of an embodiment of a cannula hub for use with the applicator assembly.

FIG. 4A is an exploded view showing a nub and its associated soft applicator cover in an embodiment of the invention.

FIG. 4B shows a nub with a soft applicator cover attached.

FIG. 4C shows the nub and applicator of FIGS. 4A and 4B with a securing collar attached.

FIG. 9 shows and exploded view of another embodiment of the invention, in which a soft applicator cover fits directly onto a syringe.

FIG. 10 shows a perspective view of the embodiment of FIG. 9.

DETAILED DESCRIPTION OF EXAMPLE EMBODIMENTS

Figure 1:
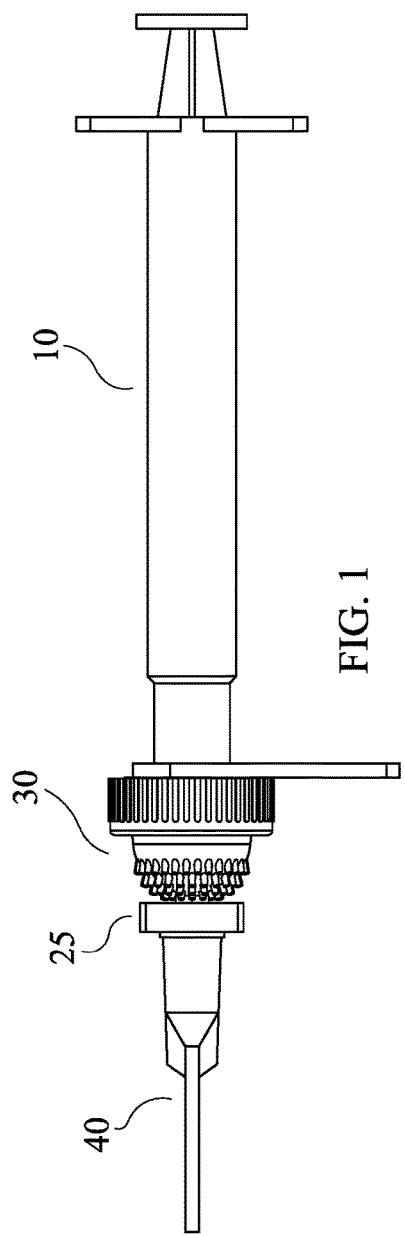
FIG. 1 is a side view of an embodiment of the applicator assembly attached to a barrel syringe.
Figure 2:
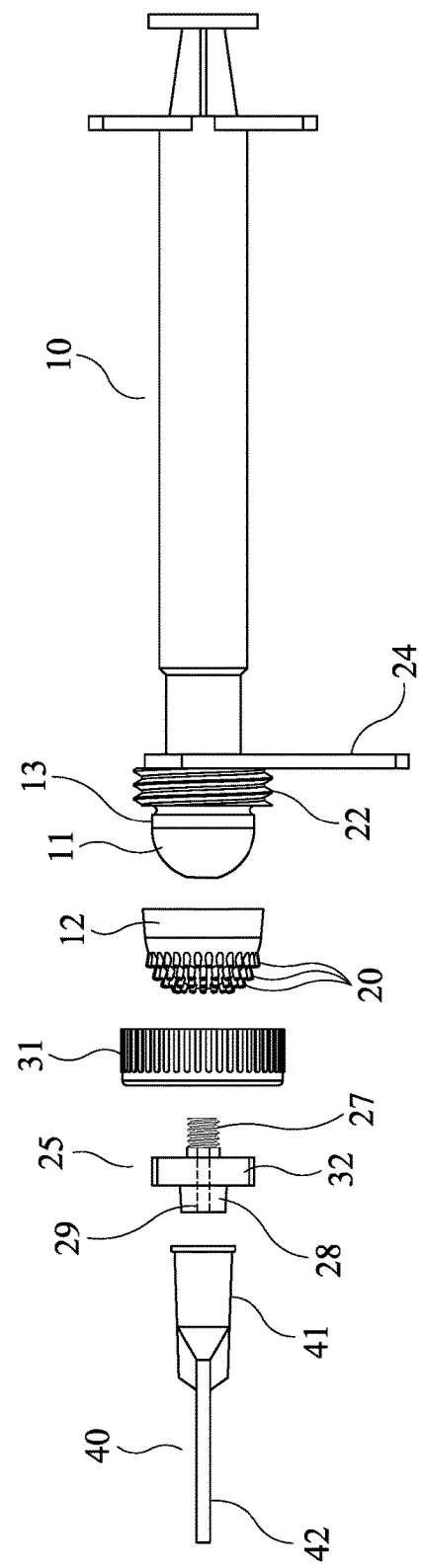
FIG. 2 is an exploded view of the assembly of FIG. 1.

An embodiment of the applicator assembly is shown in FIGS. 1 and 2. An applicator assembly 30 attaches to a barrel syringe 10, which may be a standard luer lock syringe. A connector 25 removably attaches a cannula 40, which may be a common hub-and-cannula unit, to the applicator 30.

Applicator 30 comprises an attachment nub 11 that fits into the syringe 10 and a soft applicator cover 12 that fits tightly over the nub 11 Connection of the attachment nub 11 to the syringe 10 may be by luer lock, in which the nub has a male luer configuration matching the female luer threads on the syringe. Other connections may be used, such as threading or a friction fit. To aid in stabilization, nub 11 may have a 360 degree groove 13 that matches to a 360 degree inward peripheral ridge 14 in the applicator cover 12.

The soft polymer applicator itself is a cover 12 with a rounded tip 15 that fits tightly over a hemispheric nub 11. It may be made of medical grade thermoplastic resin or medical grade silicone. It incorporates a plurality of soft filament projections, or tendrils 20, about 3/16 inch (4.75 mm) long and 0.8 mm in diameter radiating outward. These "koosh" extensions allow effective dispersion of a viscous liquid while remaining comfortable to the skin. Different filament characteristics may be employed depending on the specific use for the applicator. For example, in the event of hair restoration, a modified silicone membrane with longer, stiffer extensions may provide a means of reducing the resistance of the hair as the applicator is being moved to distribute the liquid.

The nub 11 that supports a soft tip covering 12 may be any hard material, and is preferably a plastic, such as polypropylene. See FIGS. 4A-4C. As noted, the nub 11 engages the syringe in some manner In an embodiment, a proximal cylindrical extension of the nub 11 has male luer threads 16 that fit female luer threads (not shown) on the syringe. A tunnel or lumen 17 extends through the nub, terminating in an aperture 18 for liquid flow. The applicator cover has a corresponding aperture 19. In an embodiment, a central cylindrical segment of the nub may include external threads 22 that engage threads in a securing collar 31 that helps hold the applicator cover in place. To better implement this feature, an external peripheral ridge 23 may be added to the above mentioned internal peripheral ridge in the applicator cover. An optional stand 24, which may be plastic, snaps onto the nub 11 to keep the tip off the table surface.

The distal portion of the nub is configured to optionally engage a cannula connector 25.

In an embodiment, the connector may be a two way male threaded cross shaped fitting 25, with a central segment comprising a cross bar 32, a proximal extension 27 adapted to engage female connector threads 26 on the nub 11, and a distal extension 28, adapted to engage a cannula hub 41. A lumen 29 through the connector permits liquid to pass between the nub and the cannula. Other connection means, such as friction fit to the nub, or threaded fit to the cannula hub, may be employed. Some cannula hubs have external male luer lock threads, and an appropriate configuration might incorporate corresponding female threads on the distal extension of the connector.

Figure 5A:
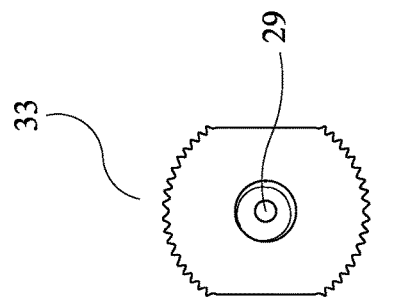
FIG. 5A shows an embodiment of a connector between the nub and a cannula hub.
Figure 5B:
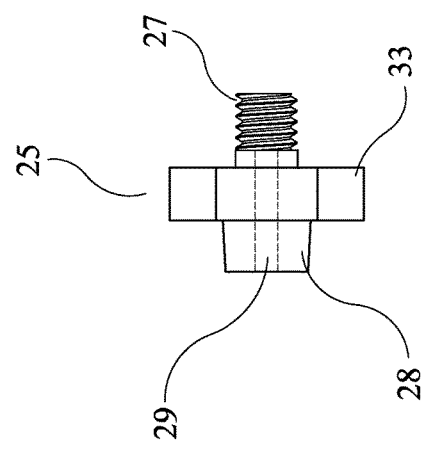
FIG. 5B shows a side view of the connector of FIG. 5A.

The cross bar 32 of the connector 25 allows the user to easily twist the connector, unscrewing it and separating the applicator tip from the cannula. The cannula connector is also sterile and removable. In a different embodiment, shown in FIGS. 5A & 5B, the connector may comprise a fitting that substitutes a partially knurled disk 33 for the cross bar.

As noted, a cannula assembly 40, comprising a cannula 42 and cannula hub 41 are attached to the distal end of the assembly. Cannula hubs of various types are known in the industry and provide a funnel-like transition from a wider aperture, such as in a syringe, to the narrow lumen of a small, usually metal, cannula. Most cannula hubs are hard plastic, but other materials, such as aluminum may be suitable. An embodiment of a cannula hub is shown in FIG. 3. The proximal end is a cylindrical chamber 43 that tapers toward its distal end. An upper flange 44 surrounds the opening and there may be male luer threads around the outside. The inner surface 45 of the chamber is smooth. The distal end 46 of the hub tapers more severely than the upper chamber, resulting in an opening that firmly engages the cannula 42 The most common cannula sizes for skin and blood applications are between 20 gauge and 12 gauge.

In operating the device, cannula 42 may be used to draw liquid into syringe 10 and may then be disengaged by detaching connector 25 thereby uncovering the applicator 30 for use in spreading the syringe contents onto the skin.

Figure 6:
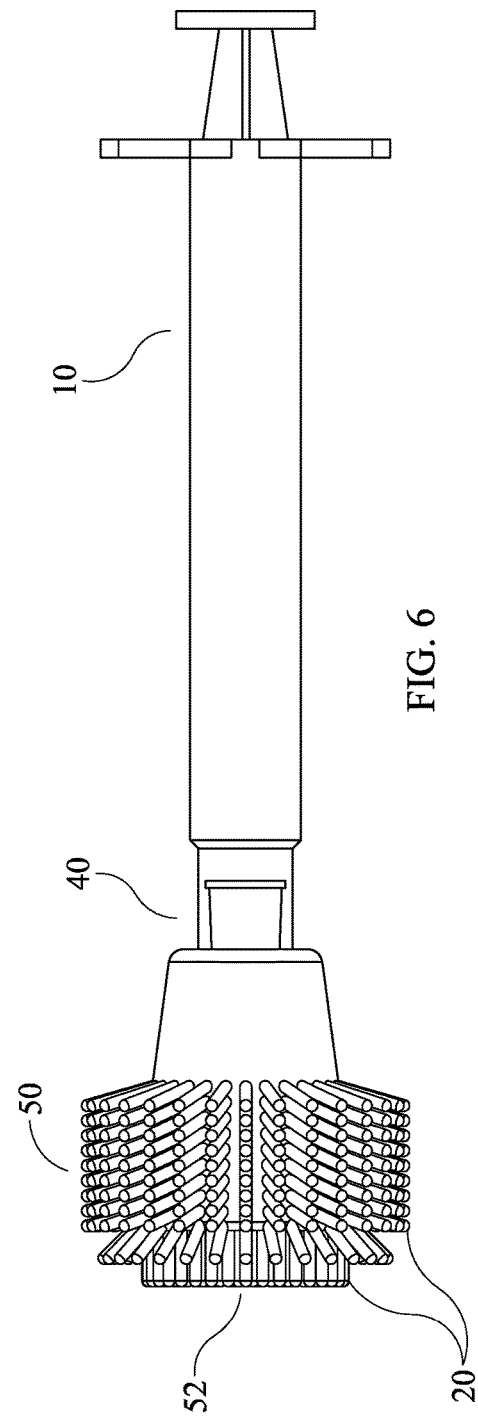
FIG. 6 shows another embodiment of the invention, in which a soft applicator cover fits over a cannula and hub attached to a syringe.
Figure 7:
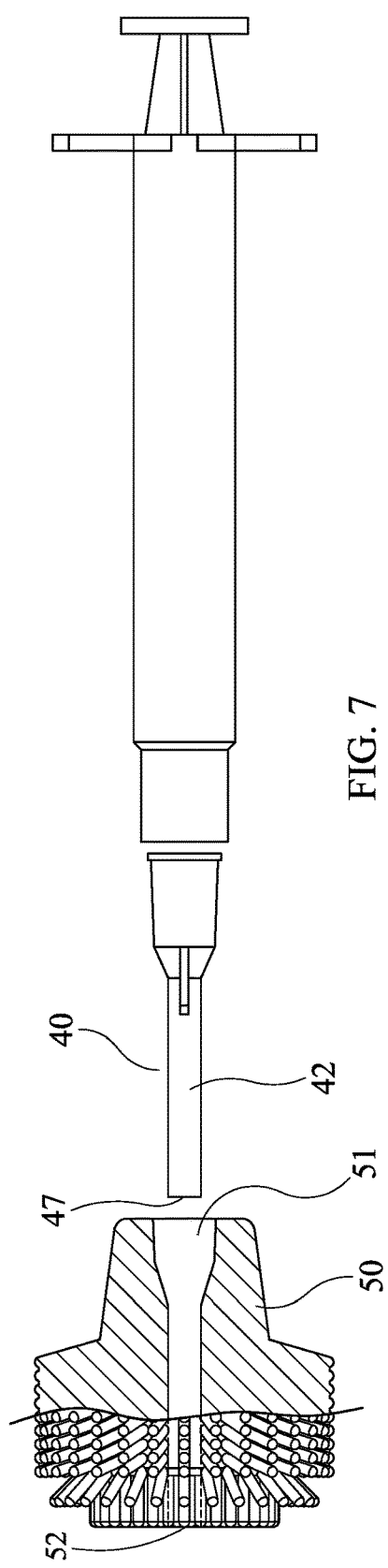
FIG. 7 shows an exploded view of the embodiment of FIG. 6 with a portion of the applicator cut away.
Figure 8:
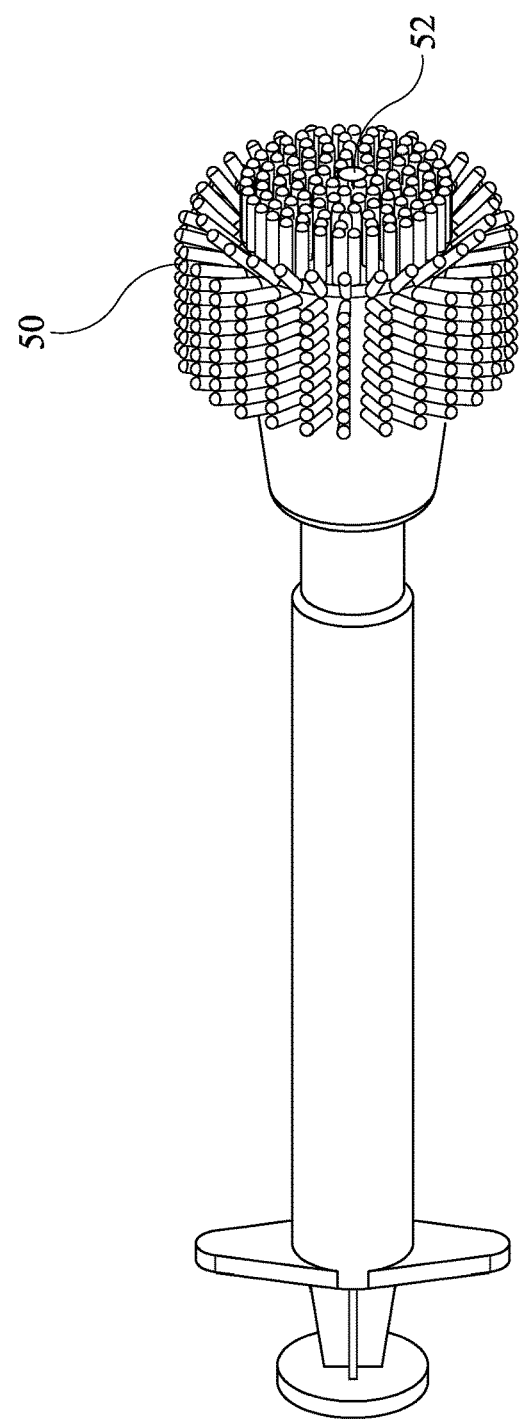
FIG. 8 shows a perspective view of the embodiment of FIG. 6.

Another embodiment of the invention is shown in FIGS. 6-8. This embodiment is useful when the user starts with prepackaged treatment liquid provided in a syringe with an attached cannula and hub. This embodiment comprises a soft applicator block 50, made of medical grade thermoplastic resin or medical grade silicone, fitted over the cannula assembly 40. Internal cavity 51 is configured to conform to the shape of the cannula assembly 40 so that it fits snugly over it. The cavity extends to an aperture 52 in the distal end of the block, having a diameter approximately that of the associated cannula. The cavity is configured so that distal end 47 of cannula 42 is stopped about ⅛" short of aperture 52. This allows the user to affix a syringe of medicine, cosmetic liquid or blood product to the sterile applicator tip and apply the contents to the skin via the "koosh ball" type 3/16" extension tendrils 20 through aperture 52. It also protects the skin by stopping the end of the cannula about ⅛" above the skin surface.

Another embodiment of the invention is shown in FIGS. 9 & 10. This embodiment is similar to the embodiment in FIG. 7, except that the soft applicator 60 is configured to fit over the tip of the syringe itself The soft applicator 60 includes a lumen 61 that aligns with the output aperture of the syringe.

The foregoing description has been presented and is intended for the purposes of illustration and description. It is not intended to be exhaustive nor limit the invention to the above teachings. The embodiments were chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out the invention.

What is claimed is:

1. An applicator for spreading liquid from a syringe onto a surface, comprising
    a hemispheric nub with a central lumen, the nub being removably attachable to the syringe;
    a soft polymer applicator cover over the nub, having a plurality of flexible tendrils and an aperture aligned with the lumen of the nub;
    a cannula hub; and
    a connector for removably attaching the cannula hub to the nub, comprising a central segment for grasping and turning the connector, a proximal extension for removable attachment to the nub, and a distal extension that removably attaches to the cannula hub.

2. The applicator of claim 1 further comprising a syringe.

3. An applicator for spreading liquid from a syringe onto a surface, comprising
    a hemispheric nub with a central lumen, the nub being removably attachable to the syringe; and
    a soft polymer applicator cover over the nub, having a plurality of flexible tendrils and an aperture aligned with the lumen of the nub;
        wherein the nub further comprises a proximal extension with luer threads for engaging the syringe and a central portion with external threads removably engaging a securing collar; and the applicator cover further comprises an external peripheral ridge around a proximal end.

4. The applicator of claim 1 further including a removable stand.

5. The applicator of claim 3 further including a removable stand.

* * * * *